United States Patent [19]

Thornton et al.

[11] 4,275,744

[45] Jun. 30, 1981

[54] AUDITORY RESPONSE DETECTION METHOD AND APPARATUS

[75] Inventors: Aaron R. Thornton, Boston, Mass.; Jerry Obenour, Sherman, Tex.

[73] Assignee: Wisconsin Alumni Research Foundation, Madison, Wis.

[21] Appl. No.: 95,552

[22] Filed: Nov. 19, 1979

[51] Int. Cl.³ .............................................. A61B 5/00
[52] U.S. Cl. ...................................... 128/731; 128/746
[58] Field of Search ......................... 128/731, 746, 902

[56] References Cited

U.S. PATENT DOCUMENTS

| 3,498,287 | 3/1970 | Ertl | 128/731 |
| 3,579,138 | 5/1971 | Harris et al. | 128/902 |
| 3,799,146 | 3/1974 | John et al. | 128/746 |
| 4,083,365 | 4/1978 | Yancy | 128/731 |
| 4,092,981 | 6/1978 | Ertl | 128/731 |

OTHER PUBLICATIONS

Thornton et al. "Journal of Speech and Hearing Research", vol. 20, No. 1, Mar., 1977, pp. 81-94.

Skinner et al. "Journal of Speech and Hearing Disorders", vol. 42, 1977, pp. 179-198.

*Primary Examiner*—William E. Kamm
*Attorney, Agent, or Firm*—Isaksen, Lathrop, Esch, Hart & Clark

[57] ABSTRACT

Auditory tone burst signals are supplied to the ear of a human subject and the electroencephalographic responses are monitored, filtered, and provided to a sampler which samples the polarity of the EEG signal at predetermined times after the auditory signal has been applied. The existence of an expected response waveform of a definite shape and frequency in an individual who responds to the sounds causes a statistical shift of the ratio of sample polarities matching the expected polarity with respect to the total number of trials. The number of matched response polarities and the number of trials are counted and can be compared after the test is completed. A decision can be made as to whether a subject is responding by selecting a statistical confidence limit which allows the hypothesis that a subject is not responding to the auditory signal to be rejected if the ratio of responses to trials falls above the selected confidence limit.

22 Claims, 5 Drawing Figures

RESPONSE PROBABILITY 4,275,744

AUDITORY RESPONSE DETECTION METHOD AND APPARATUS

BACKGROUND OF THE INVENTION

1. Field of the Invention

This invention pertains generally to the field of test procedures and apparatus used to determine whether hearing impairment exists in an individual without the voluntary response of the subject.

2. Description of the Prior Art

Detection of hearing impairment in an individual usually takes place as the individual matures and it is observed that he or she is not responding normally to aural stimuli. A child may be several years old before his hearing impairment is fully recognized, and his educational development will have been consequently delayed and possibly permanently impaired. It is therefore highly desirable to screen children at as young an age as possible, preferably soon after birth and before they are initially released from the hospital. However, it is obvious that babies cannot voluntarily communiate with the person who examines them and thus some other means must be found to determine whether the baby is hearing an auditory signal.

It has been found that the presence of certain audible signals will produce changes in the electroencephalographic (EEG) signals of a person whose brain is in fact responding to a sound detected by the person's ears. Unfortunately, the response signals present in an electroencephalogram are relatively small in magnitude compared to general EEG brain activity levels. Techniques such as signal averaging have been used for diagnostic evaluations to separate the response signal from the background noise, but the equipment required is relatively expensive and a fairly high level of personnel training is required for reliable identification and interpretation of the average response waveform. While the time and cost involved for such tests can be justified for diagnostic purposes, they are not practical for mass screenings.

SUMMARY OF THE INVENTION

It has been determined that the electroencephalographic waveforms seen in response to certain types of aural signals are consistent across individuals in shape and frequency, even though the response signals may be buried within the background EEG signal and not readily observable. In accordance with the invention herein, it was determined that observations of the EEG signal made at selected intervals following an auditory stimulus can provide a statistical estimate of the likelihood of a response being present in the individual tested.

The apparatus of the invention includes a stimulus generator which provides a train of audio frequency pulses to an earphone applied to the ear of the person being tested. While various stimulus waveforms may be used, a series of tone bursts is preferred. Each pulse evokes a characteristic response in the EEG waveforms of the subject. The shape and frequency of response waveforms for many types of stimuli are known, or can be determined.

The apparatus further utilizes an electroencephalographic transducer attached to an individual to receive the pertinent brain waves. The EEG signal is then preferably transmitted through a signal conditioner which stabilizes the average magnitude of the signal and filters out signal components above and below the range of frequencies of interest. The conditioned signal is then applied to a signal sampling device which samples the signal at predetermined times after the time of application of the auditory signal and provides a response output pulse when the polarity of the sample signal matches the expected polarity at the predetermined times. The expected polarities are based on a priori knowledge of the typical response waveforms. The sampling means also provides a series of trial output pulses corresponding to each sample time, whether a response pulse is produced or not.

A response counter counts the number of response pulses over the period of the test while a trial counter counts the total number of trials during this period. The test can be terminated either when the number of responses (matches between actual and expected polarities at the sample times) or the number of trials reaches a predetermined level. The number of responses and the number of trials are displayed to the operator, and the ratio of responces to trials can be utilized by the operator to determine the likelihood that the individual is in fact responding to the audio stimulus.

For example, if the EEG signal was entirely random and unbiased, the expected value of the responses to trials ratio would be 0.5. In an individual who was responding to the auditory stimulus, the ratio will be greater than 0.5. A decision as to whether a certain ratio indicates that a response to the auditory signal is present can be made to a statistical confidence level. A sufficient number of trials can be run to provide a statistical estimate within a relatively short time, in the range of one to four minutes.

The use of the apparatus requires very little training on the part of the operator of the apparatus since his function is limited to attachment of an earphone and EEG electrodes and initiation of testing. The responses to trials ratio provides a simple numerical criterion by which individuals who show a probability of hearing impairment can be selected for further diagnostic testing.

Further objects, features and advantages of the invention will be apparent from the following detailed description and the accompanying drawings.

DESCRIPTION OF THE PREFERRED EMBODIMENT

Figure 1:
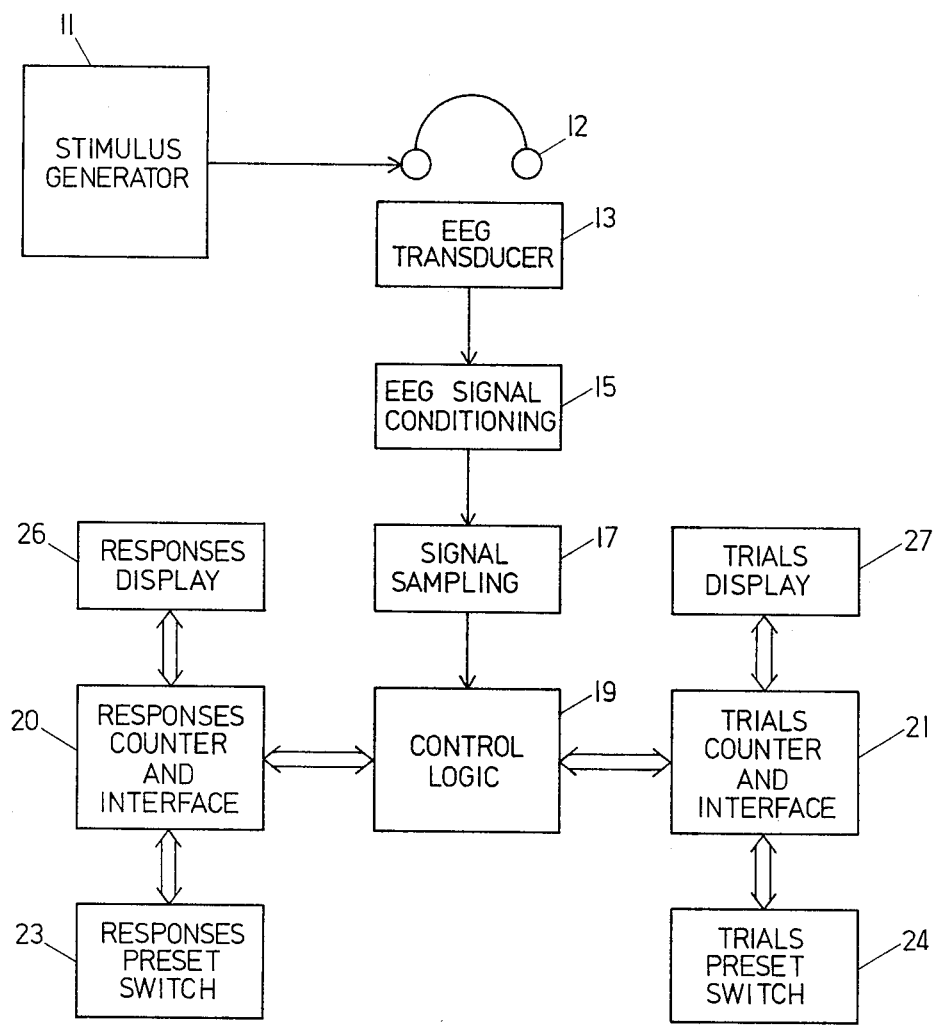
FIG. 1 is a schematic block diagram showing the functional units of the invention.

With reference to the drawings, a block diagram showing the functional units of the apparatus of the invention is shown in FIG. 1. A stimulus pulse train generator 11 provides a series of pulses to an earphone 12 which is placed on one ear of the individual to be tested. Various types of stimuli can be used, including tone bursts of various frequencies and square wave pulses. We have found that particularly good results are obtained with a series of pulses comprising 1,000 Hz tone bursts having a pulse width of approximately 8.5 milliseconds, 2 milliseconds ramp rise and decay times, and a pulse frequency of approximately 12.5 Hz. The responses of the individual are detected by an electroencephalographic (EEG) transducer 13 which preferably includes a vertex electrode referred to the ipsilateral earlobe with a forehead ground. A standard EEG transducer and pre-amplifier system may be utilized.

The electroencephalographic signal from the transducer 13 is provided to an EEG signal conditioner 15 which stabilizes the average magnitude of the EEG signal and filters out signal components above and below the range of frequencies of interest. For example, the middle component waveform of the electroencephalographic response of adults to 1,000 Hz tone bursts includes a characteristic response waveform component having a dominant frequency of about 45 Hz. Since EEG signal frequencies above and below this "template" waveform frequency are not of interest, the signal conditioner 15 includes a bandpass filter which passes the relevant signal but filters out higher and lower frequencies. The filter may have a low frequency break point of from 25 to 35 Hz to filter out the major extraneous signal energy which is concentrated at lower frequencies, and an upper frequency break point of 100 Hz to 120 Hz to filter out high frequencies which interfere with proper sampling, as explained below. It is apparent that by filtering out the higher and lower frequencies of the EEG signal, the expected response signal will comprise a greater proportion of the overall signal, or in other words, the signal to noise ratio will have been improved. However, it is observed that even after filtering, the "noise" or extraneous information signal is still very large with respect to the magnitude of the expected response signal, and the presence of a response signal cannot easily be detected.

Figure 2:
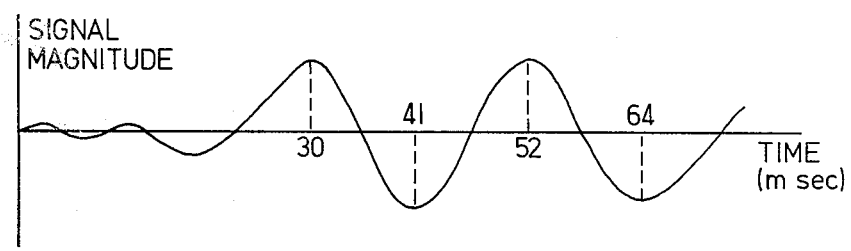
FIG. 2 is an example of an evoked response waveform as it would be seen if separated from the other components of an EEG signal.

An illustrative graph representing the portion of an exemplary EEG response in adults due to a 1,000 Hz pulse is shown in FIG. 2. After an initial delay following initiation of the auditory pulse (the zero time coordinate position) the waveform builds up to a relatively steady 45 Hz signal which lasts two or three cycles before damping out. The waveform illustrated in FIG. 2 is that which would be observed at the output of the signal conditioner 15, and is phase shifted from the input signal phase because of the phase shift associated with the bandpass filter. For the filter embodiment described below, the response waveform is observed to have peaks at approximately 30, 41, 52, and 64 milliseconds after the initiation of the auditory test pulse. The shape and frequency of the waveform has been found to be remarkably constant across individuals within an age group who can hear the auditory signal. The corresponding waveform peaks observed in infants are found to occur at slightly different times, i.e., 28, 38, 54 and 71 milliseconds after the test pulse.

To detect the presence or absence of a waveform of the form shown in FIG. 2, the conditioned signal from the signal conditioner 15 is supplied to a signal sampling unit 17. The signal sampler 17 is synchronized with the pulses delivered by the stimulus generator 11 so as to sample the magnitude of the EEG signal at discrete times after initiation of the audio signal, for example, at times corresponding to the 30, 41, 52, and 64 millisecond peaks in the waveform of FIG. 2. The signal sampler provides a response output pulse when the polarity at the sampling time matches the expected polarity of the template waveform shown in FIG. 2. The signal sampler 17 also provides a trials output pulse at each time at which a sample is taken so that the total number of trials can be counted.

Although the maximum amplitude of the four major peaks in the response waveform shown in FIG. 2 will be approximately 20 dB below the peaks in the filtered EEG signal, when the response waveform is present, it has a probabilistic effect on the EEG signal at the times of the expected peaks in the response waveform. For example, if the EEG signal from the signal conditioner 15 was random and unbiased, the probability of the sampling unit 17 measuring either a positive or negative voltage at the sample times would be 0.5. However, when the audio response waveform is present within the EEG, it will shift the probability of measuring the expected polarity to some value above 0.5.

The response pulses and the trial pulses are transmitted through a control logic block 19 which controls the distribution of the pulses to a responses counter and interface block 20 and a trials counter and interface block 21. The response counter receives the output pulses from the signal sampling unit through the control logic and counts the pulses received by it until the counter is instructed to terminate counting. Similarly, the trial counter 21 receives the trial output pulses from the sampler through the control logic and counts the pulses received by it over the period of the test until the counter is instructed to terminated counting. Termination of counting may be accomplished by the use of a preset responses limiting switch 23 or a preset trial limiting switch 24. These switches monitor the count that is accumulating in the responses or trials counter, and one or the other will provide a control signal to the counter and to the control logic to cause termination of counting when either the number of responses or the number of trials has reached a predetermined limiting number which has been selected by the operator. The count total in the response counter is transmitted to and displayed on a responses display unit 26, and the number of trials are displayed to the operator on a trial display unit 27. From the numbers shown on these displays, the operator can calculate the ratio of responses to trials and utilize this information to make a decision as to whether or not a response was in fact present in the individual. This decision cannot be made with certainty, but can be made to a statistically determinable level of confidence.

Figure 3:
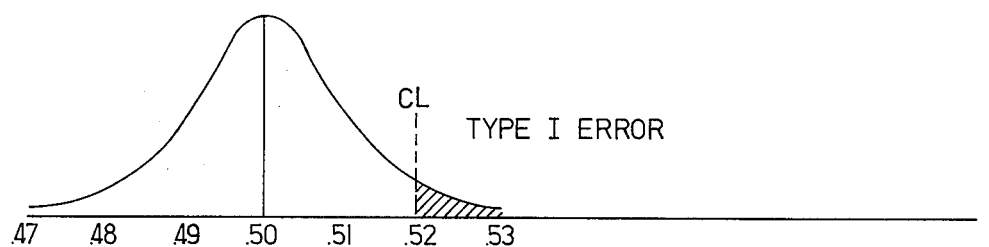
FIG. 3 is an illustrative graph of probability distributions for a hypothetical response.
Figure 3:
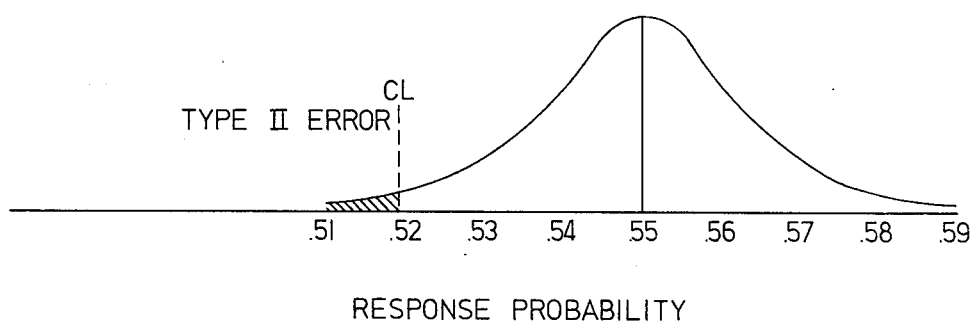

For example, if it is assumed that the sample of the polarities of the EEG signal follows a binominal probability distribution, then the mean of the random variable having such a distribution is the number of samples (n) times the probability of selecting a sample of that polarity ($\theta$). The variance will be $n\theta(1-\theta)$. If the EEG signal was random and unbiased, one would expect that the probability of either a positive or negative polarity would be 0.5, and for a run of 3,000 trials, the means of the probability distribution would be 1,500 and the standard deviation would be 27.4. Because the number of samples is large, the binominal distribution can be approximated by a normal distribution having the same mean and standard deviation. This approximated normal distribution is shown by the upper curve in FIG. 3. An arbitrary confidence level can be choosen and the null hypothesis that no response is present can be rejected if the ratio of responses to trails is above the confidence limit. The risk of rejecting the null hypothesis, when in fact no response is present, or the Type I error, is the probability contained in the tail of the probability function above the confidence limit.

It should be noted that the filtering or the EEG signal will tend to bias the background EEG signal so that the expected variance of the responses to trials ratio can be somewhat greater than the binomial computation. This bias increases as the passband of the filter is narrowed, thus limiting the extent to which the signal to noise ratio may be improved without significantly degrading the statistical accuracy of the sampling.

The setting of the confidence limit to minimize Type I error also introduces the possibility of a Type II error in which the hypothesis of a response being present is rejected when a response is in fact present, simply because the ratio of responses to trials falls below the arbitrarily choosen confidence limit. The probability of Type II error is the probability contained under the tail of the actual responses probability distribution which lies below the confidence limit, as illustrated on the lower propability curve of FIG. 3. The mean of the assumed normal probability distribution for the response to trials ratio of all persons having normal auditory responses may be estimated by testing a number of subjects with normal hearing. As an example, the estimated ratio mean for adults at moderate audio signal levels was found to be approximately 0.55. The variance of the distribution is greater than that of the approximated binomial distribution due to the response variation that is encountered among subjects. Since the confidence limit is fixed to satisfy the criteria for Type I error, and the mean of the response distribution is primarily a characteristic of the signal to noise ratio of the response within the filtered EEG signal, the only means to control the probability of Type II errors is the variance of the response distribution, which is inversely related to the number of trials. For the stimulus signals described above, which provide about 50 trials a second, we have found that accumulating 3,000 trials over a minute of testing ordinarily is sufficient to demonstrate that a response is present to less than a 5% risk of Type I or Type II errors.

Where the ratio of responses to trials is fairly close to, but still greater than, 0.5, the confidence limit cutoff line for Type I errors may yield a risk of Type II errors substantially greater than 5% if only 3,000 trials are taken. However, the trials can ordinarily be extended for 2 or 3 more minutes to accumulate enough trials to decide to at least a 5% confidence level that a response either is or is not present. It is noted that, as the number of trials increases, the standard deviations of the binomial distribution and the response probability distribution decrease while the spread between the mean of the binominal distribution and the estimated mean of the response distribution remains the same.

Figure 4A:
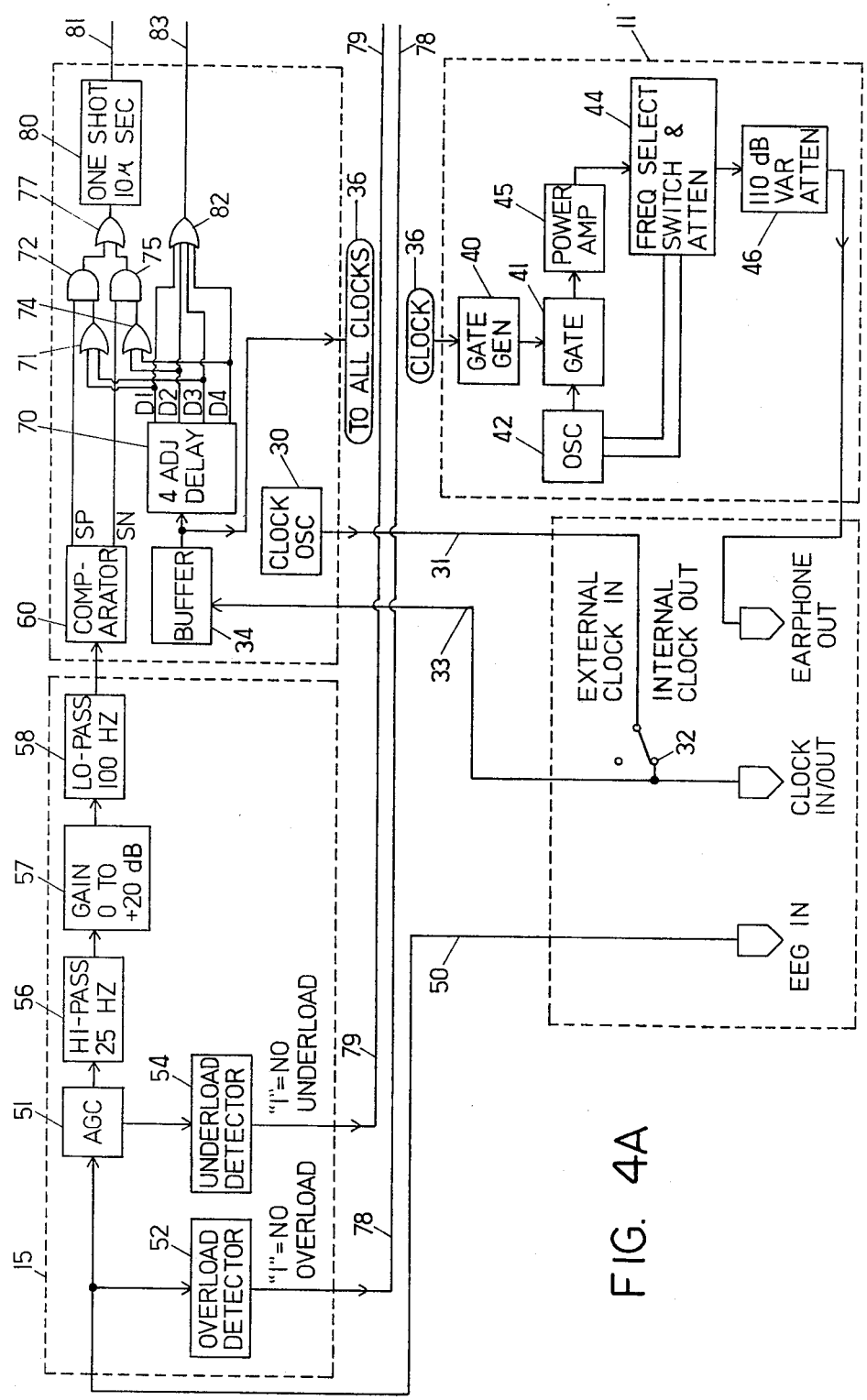
FIGS. 4A and 4B are schematic diagrams of the operational components of the apparatus.
Figure 4B:
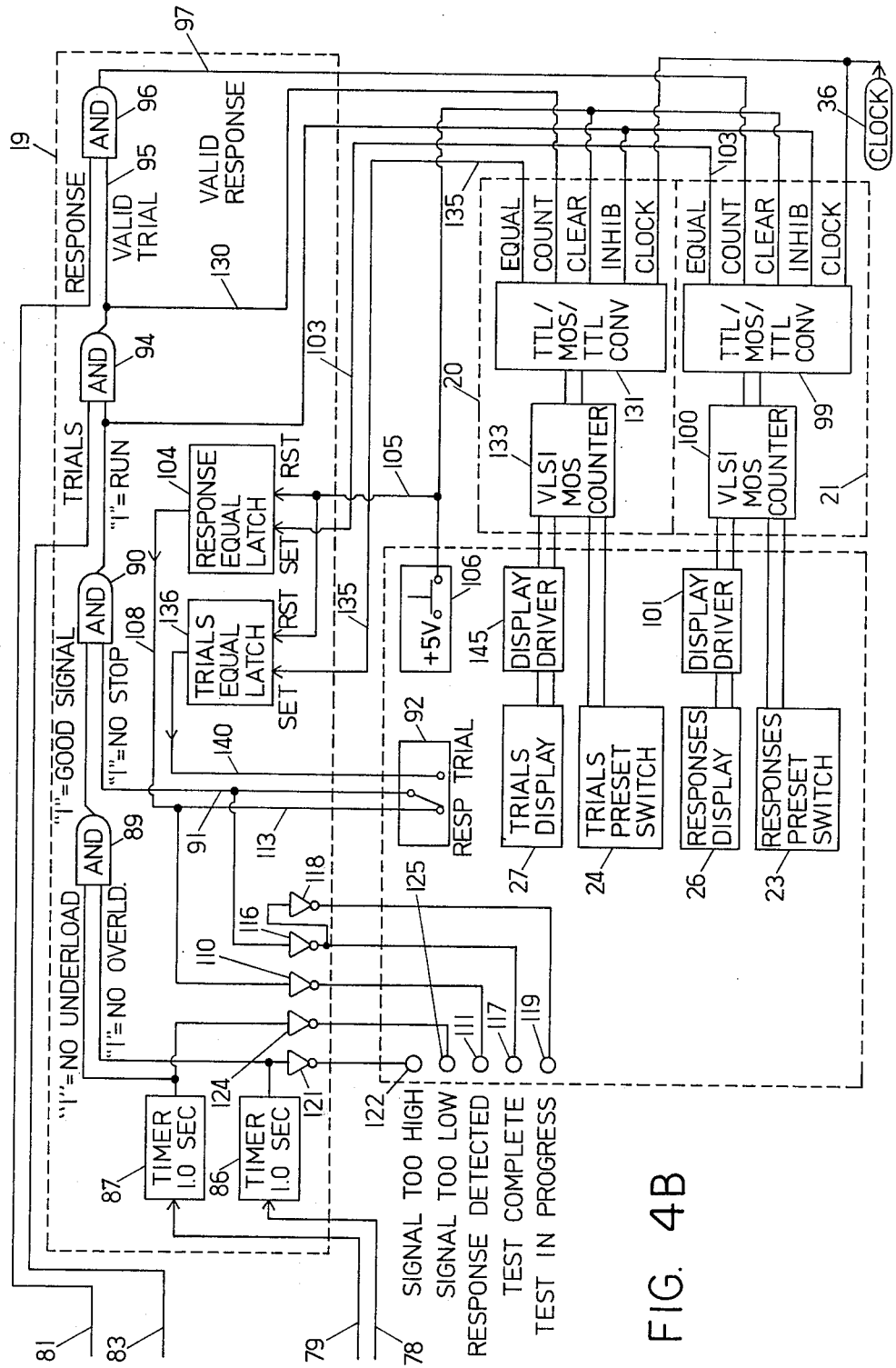

Details of the logic utilized in the apparatus of the invention are shown in the views of FIGS. 4A and 4B. A master clock oscillator 30 provides a regular series of rectangular clock pulses, for example at a frequency of 12.5 Hz with a one millisecond pulse width, through an output line 31 to a switch 32 which allows the operator to select between the internal clock and an external oscillator. The clock pulses are thence transmitted along a line 33 to a buffer unit 34 which amplifies and isolates the clock signals from the rest of the system to prevent overloading of the clock oscillator. The buffered clock pulses are transmitted on a line 35 through connectors 36 to the other components of the apparatus.

The clock pulses from the connector 36 are supplied to a gate generator 40 within the stimulus generator 11. The gate generator provides shaped output pulses corresponding to the envelope of the tone burst stimuli to be provided to the earphone, with each pulse from the gate gnerator being triggered by a clock pulse. As indicated above, a tone burst having a pulse width of 8.5 milliseconds with 2 milliseconds ramp up rise and ramp down decay times has been found to be satisfactory. The ramp rise and decay of the pulses are preferred in order to avoid having substantial high frequency components associated with the pulses. The pulses from the gate generator 40 are provided to an electronic gate 41 which transmits a sine wave signal from an audio oscillator 42 at a magnitude proportional to the gating pulse. The audio oscillator is preferably capable of providing variable frequencies which are selected by a frequency select switch 44, with a preferred audio frequency being in the range of 1,000 Hz. The tone bursts passed through the gate 41 are transmitted to a power amplifier 45 and thence through an attenuator contained within the frequency select switch unit 44 to a variable attenuator 46, and the attenuated signals are supplied to the earphone 12. The attenuator 46 allows the volume of the audible stimulus signal to be varied, thereby allowing tests to be made on a subject to determine the relative degree of hearing impairment. The oscillator may also be chosen to be capable of providing variable frequencies to allow a measurement of the response of the subject to sounds of different frequencies.

The output received from the EEG transducer is transmitted on an input line 50 to an automatic gain control circuit 51 and an overload detector 52, both contained within the EEG signal conditioning portion 15. The overload detector maintains a "high" output as long as no overload is detected, and is included in the circuit to prevent data being taken during times when the EEG signal is very large, since this condition will correspond to a very poor signal to noise ratio.

The automatic gain control unit 51 is of standard construction utilizing commercial integrated circuit packages such as an LM 370. The purpose of the automatic gain control unit is to standardize the average magnitude of the incoming EEG signal so that the signal presented to the sampler 17 is large enough in magnitude to be within the sensitivity of the sampler but not so large as to overload or saturate the sampler. The automatic gain control 51 also provides an output to a sensing unit 54 which detects underloads, that is, signal levels which are so low that they are indicative either of a malfunction in the EEG transducer or the presence of transient periods of low level signals that would not provide statistically significant inputs. The output of both the overload detector 52 and the underload detector 54 are preferably maintained in a "one" or high state as long as no overload and no underload exist. The outputs are transmitted to the control logic 19, and, as explained in further detail below, the control logic may block the counting of responses and trials when either an overload or an underload is present.

The stabilized EEG signal from the automatic gain control unit 51 is passed through a high pass filter 56 (shown illustratively with a 3 dB lower frequency cut-off at 25 Hz), and then to a variable gain amplifier 57 which provides signal gain and isolation with a variable gain of 0 to 20 dB. The amplified signal from the amplifier 57 is passed to a low pass filter 58, which for illustrative purposes is shown having a 3 dB upper frequency cut-off 100 Hz. The filters preferably have a very steep roll off, e.g., 48 dB per octave, and may be of standard Butterworth design. As indicated above, the filtering out of high and low frequencies on either side of the expected response frequency is desirable, although not essential, since it improves the signal to noise ratio of the resultant signal.

The conditioned signal is passed to a comparator 60 within the signal sampling unit 17. The comparator 60 has two outputs lines, labeled SN and SP in FIG. 4, with a high output being present on the SP line if the signal presented to the comparator is positive, a low output being provided on the SP line otherwise; and similarly a high output being presented on the SN line if the signal presented to the comparator is negative, and a low output presented on the SN line otherwise. The buffered clock pulses from the buffer unit 34 are supplied to an adjustable delay circuit 70 which provides a train of four pulses at preselected times after the time at which a tone burst is supplied by the stimulus generator 11. The adjustable delay circuit 70 is of standard design and has four output lines labeled D1, D2, D3, and D4. For example, the delay circuit may comprise four pair of 555 timers, with the first of each pair of timers being triggered by the clock pulse to provide an output pulse whose length corresponds to the delay desired, and with the second timer in each pair triggering on the trailing edge of the pulse from the first timer to provide an output pulse of uniform duration. The adjustable delay provides a pulse on the line D1 at a selected period of time after initiation of the tone burst which corresponds to the first peak in the expected EEG waveform, e.g., for the response signal waveform shown in FIG. 2, at 30 milliseconds after initiation of the tone burst. The length of each pulse produced by the adjustable delay units may be in the range of 10 microseconds. Similarly, pulses would be produced on the output lines D2 at 41 milliseconds, D3 at 52 milliseconds, and D4 at 64 milliseconds. The outputs on lines D1 and D3 are provided to a OR gate 71 whose output is provided to an AND gate 72 wherein it is ANDed with the signal on the line SP; the AND gate 72 will thus produce an output pulse if and only if the EEG signal is positive at 30 milliseconds of 52 milliseconds after the tone burst. Similarly, the output lines D2 and D4 are provided to an OR gate 74 and the output thereof is provided to an AND gate 75 with the output line SN such that the output of this AND gate is positive if and only if the EEG signal is negative at 41 milliseconds or 64 milliseconds after the tone burst. The outputs of the two AND gates 72 and 75 are thereafter provided to an OR gate 77 and the output of this gate is provided to a "one shot" multivibrator 80 which is illustratively shown as having a 10 microsecond pulse length. The one shot 80 provides a uniform output pulse on the output line 81 which is provided to the control logic 19, and ensures that changes in the output of the comparator 60 during a sample pulse do not cause spurious pulses to be transmitted to the counters.

An OR gate 82 receives all of the delay output lines D1–D4 and provides a High output on an output line 83 whenever a pulse is present on any of the lines D1–D4.

The outputs of the overload detector 52 and the underload detector 54 are provided on output lines 78 and 79 to the control logic unit 19, wherein the output signals from these detectors are supplied respectively to time delay units 86 and 87. Each of the time delay units provides an output at a high or "one" value as long as the input to the timer is high. When the input to the timer drops to a low or "zero" value, the timer will continue to maintain a high output for one second, and then drop its output to a low or "zero" level if the input to the timer does not go high again within the one second time delay. The output of the two timers 86 and 87 are inputed to an AND gate 89 the output of which is provided to another AND gate 90. The output of the AND gate 89 will remain at a high or "one" level as long as a consistent no overload or underload EEG input signal is received. The other input of the AND gate 90 is received on a line 91 from a selector switch 92 which allows the operator to select between a mode in which the test is stopped when a certain number of responses is reached, or mode in which the test is stopped after a selected number of trials is reached. The output of the AND gate 90 is provided to one of the inputs of another AND gate 94 whose other input is the output line 83 from the OR gate 82. A high output of the AND gate 94 indicates that a valid trial exists at that point in time, and this output is supplied to yet another AND gate 96 which receives its other input from the output line 81 carrying the response pulses. Thus, an output will be present on the output line 97 from the AND gate 96 only when (1) a high level exists on the output line 95 from the AND gate 94 indicating that a valid trial has taken place, and (2) a pulse is present on the line 81 indicating that an expected signal polarity has been found.

The output line 97 is presented to one of the inputs of a TTL/MOS/TTL interface converter 99, such as a 7406 hex inverter, which converts the TTL output signal present on the line 97 to a signal compatible with CMOS integrated circuitry. The response pulses are transmitted from the interface converter 99 to a large scale integrated circuit CMOS counter 100 which is available as an integrated circuit package of standard construction. The counter 100 counts the number of response pulses and transmits the coded output to the response preset switch 23. The response count output is also transmitted from the counter 100 to a display driver 101 which provides the output power necessary to drive the response display 26, which may be in the form of a LED display or other visible output.

The response preset switch 23 may consist of binary coded dial switches which are set by the operator to predetermined number. The dial switches receive the digit position output from the counter and return a binary coded signal to the counter which is indicative of the number to which the switch is dialed. The counter compares the coded signal from the switches with its internal count. When the count within the counter 100 reaches the preset number, the counter transmits a high output signal on its "EQUAL" output line through the interface converter 99 and thence to a output line 103 which is provided to the set input of an RS Flip-Flop 104. The reset input of the Flip-Flop 104 is connected to a line 105 leading to a start switch 106. At the start of the test, the operator presses the switch 106, which provides a five volt high level on the line 105 to reset the Flip-Flop 104 which thereafter maintains a high or "one" output on the inverted output line 108. When a pulse is provided on the output line 103 from the interface converter unit 99, it sets the Flip-Flop 104 to its low or "zero" state at its inverted output. The low signal on the line 108 is provided to an inverting amplifier 110 which supplies a high voltage level to an indicator light or LED 111 mounted on the face of the unit.

A connecting line 113 is tapped off the output line 108 to the mode select switch 92, such that when the mode select switch is in the response stop position, a high signal presented on a line 113 will be transmitted along the output line 91 to the AND gate 90. A high or logic level "one" signal will be present on the line 91 as long as the Flip-Flop 104 remains in its reset state. A pulse on the set input to the Flip-Flop 104 will cause the inverted output 108 to be set to a low level, which will cause the output of the AND gate 90 to drop to a low or logic "zero" state and cause the outputs of the AND gates 94 and 96 to drop to a low or logic "zero" state, thereby terminating the supply of pulses to the trials and responses counters. A low state on the line 19 will also be presented to an inverting amplifier 116, which lights an indicator light 117 to tell the operator that the test has been completed. The output of the amplifier 116 is also provided to the input of another inverting amplifier 118 which will provide power to an indicator lamp 119 as long as the input to the amplifier 118 is low. The lighting of the lamp 119 tells the operator that the test is still in progress, and is the complement of the indicator lamp 117.

The output of the timer 86, which receives the overload detection signal from the overload detector 52, will remain high as long as the input to the timer remains at a high level or a logical "one." A high level output from the timer is presented to an inverter 121 which in turn is connected to a signal lamp 122. When the output of the timer 86 drops down to its low state, the output of the inverter 121 will go high to drive the lamp 122 to indicate to the operator that too large an EEG signal is being received. Conversely, the output of the timer 87 is provided to the input of an inverter 124 which is connected to a signal lamp 125. A low output from the timer 87 will cause the inverter 124 to provide a high output to light the signal lamp 125 and thus indicate to the operator that the EEG signal being received is too low.

The output pulses on the line 95, with each pulse representing one trial, are transmitted on a branch line 130 to the counting input of a TTL/MOS/TTL interface converter 131. The interface 131 converts the TTL logic signals present on the line 130 to pulses compatible with a CMOS counter 133 which maintains a running count of each trail input pulse presented to it. The coded output of the counter is provided to the trials preset switch 24, similar to the switch 23, which allows the counter 133 to compare the running total of trials to a preset number which has been dialed into the switch by the operator. When the number of pulses counted by the counter 133 reaches the predetermined total, the counter provides an "EQUAL" signal through the interface unit 131 to an output line 135 and thence to the set input of an RS Flip-Flop 136.

The reset input of the Flip-Flop 136 is connected to the line 105, which in turn is connected to the start switch 106, such that the pressing of the start switch by the operator resets the Flip-Flop 106 to its initial position wherein its inverted output is high. The inverted output is provided via an output line 140 to the mode select switch 92, If the operator so chooses, he may place the mode select switch in its trail select position such that when the total number of trials is equal to the number set in the trials preset switch 24, a high or logical "one" signal will be presented on the input line 135 to the set input of the Flip-Flop 136, switching the Flip-Flop to its set position wherein the output on the inverted line 140 is at a low or logical "zero" state. The low state signal will be transmitted along the line 91 through the AND gate 90 which will terminate the test. Presentation of a low input to the amplifier 116 will cause the test complete lamp 117 to be lit, and the test in progress lamp 119 to be darkened. However, a low signal will not be provided to the amplifier 110, and therefore the response detected lamp 111 will not light.

The output of the AND gate 90 is also optionally provided to the "inhibit" inputs of the converter interface units 99 and 131. When the output of the AND gate 90 goes low, indicating that good signals are not being received, the passage of any signals through the interface units will be inhibited so that spurious pulses are not picked up by the counters.

The coded output of the counter 133 will also be provided to a display driver 145 which in turn will drive the trials display 27 on the face of the device.

As indicated above, the test can be terminated either when the responses counted are equal to a predetermined value or when the number of trails reach a limit. In either case, the number of trials and the number of responses will be displayed on the display units 27 and 23 respectively. The operator can then easily calculate the ratio of responses to trials and conclude that a response is or is not present based on the predetermined statistical confidence levels. Ordinarily, the operator would set the mode switch 92 in the trial select position and set the trial select switch 24 to terminate the test at a predetermined number of trials, for example, after 3,000 trials over a one minute period of time as described above. However, the operator may find that the ratio of responses to trials obtained after a one minute period of tests is not sufficiently greater than 0.5 to say with the required level of confidence that a response is in fact present. Therefore, the operator may rerun the tests for a longer period of time, such as three or four additional minutes, in order to increase the sample size and decrease the variance of the ratio of responses to trials. Alternatively, by selecting the response stop position of the mode switch 92, the operator can stop the test when the number of responses detected reaches a predetermined limit, thereby somewhat shortening the length of the test since the number of responses will ordinarily build up at a somewhat factor rate than one half the number of trials. In either case, it has been determined that fairly accurate decisions concerning the presence or absence of a response can be determined within a relatively short period of time, such as one to four minutes per test.

It is apparent that the number of trials need not be directly counted if the rate at which trials occur is known. For the example given above, trials accumulate at the rate of 3,000 a minute. The test can thus be terminated by the operator after a selected period of time and the approximate number of trials can be easily calculated. The test can also be terminated automatically by the apparatus after a predetermined time. Since the number of trials increases substantially linearly with time, the trials counter essentially provides this elapsed time measurement.

The logic circuitry shown in FIG. 4 can be readily packaged in a portable unit which can be utilized in the nursery environment for which it is intended, in combination with customary EEG recording equipment which is ordinarily readily available. The device is simple to use, since the operator merely has to connect the EEG electrodes to an infant in a customary manner and start the test. The device then takes the sample and provides an output to the operator after a relatively short period of time, such as a minute, whereupon the operator can immediately determine whether or not a response is likely by simply calculating the ratio of responses to trials and comparing it with the predetermined confidence limit. The confidence limit can also be expressed in terms of response totals, so that the operator need only compare the response total displayed by the unit with the predetermined response total which provides the confidence limit for the number of trials that have been run. In this way, infants, can be very simply and easily screened for potential hearing defects, with little expertise or training being required of the operator.

The method and apparatus of the invention can also be used for more detailed diagnostic purposes in both adults and babies. The variable attenuator 46 can be used to adjust the volume of auditory signals provided to the subject so that the degree of hearing impairment can be determined. The audio frequency signal provided by the oscillator 42 can also be varied to determine the response of the subject to different frequencies.

It is understood that the invention is not confined to the particular construction or details described herein, but embraces all such modified forms thereof as come within the scope of the following claims.

We claim:

1. Apparatus for generating data from which the likelihood of hearing impairment can be determined in a human subject who receives a selected auditory signal and whose response thereto is detected by an electroencephalographic transducer, comprising:
   (a) sampling means for sampling the polarity of the electroencephalographic signal at predetermined times after the time of application of the selected auditory signal which correspond to the positive and negative peaks of the waveform of the expected response component of the electroencephalographic signal, said sampling means providing a response output pulse when the polarity of the sampled signal matches the polarity of the expected response waveform at the predetermined time and also providing a trial output pulse at the time of each sample;
   (b) synchronizing means responsive to the auditory signal for triggering the sampling means at the appropriate predetermined times;
   (c) a response counter receiving the response output pulses from said sampling means and counting the pulses received by it and providing an output signal which is indicative of the total number of pulses counted; and
   (d) a trial counter receiving the trial output pulses from said sampling means and counting the number of pulses received by it and providing an output signal indicative of the total number of pulses counted, whereby an operator can determine the ratio of the number of response pulses to the number of trial pulses over a selected period of time to provide a measure of the likelihood that a response is being evoked in a subject by the auditory signals.

2. Apparatus for generating data from which the likelihood of hearing impairment can be determined in a human subject who receives a selected auditory signal and whose response thereto is detected by an electroencephalographic transducer, comprising:
   (a) an auditory stimulus generator adapted to provide auditory signal pulses to the ear of the human subject at a known uniform frequency;
   (b) sampling means for sampling the polarity of the electroencephalographic signal at predetermined times after the time of application of the selected auditory signal which correspond to the positive and negative peaks of the wave form of the expected response component of the electroencephalographic signal, said sampling means providing a response output pulse when the polarity of the sampled signal matches the polarity of the expected response waveform at the predetermined time;
   (c) synchronizing means responsive to the auditory stimulus generator to trigger the sampling means at the predetermined times after the auditory signal; and
   (d) a response counter receiving the response output pulses from said sampling means and counting the pulses received by it over a selected period of time and providing an output signal which is indicative of the total number of pulses counted, whereby an operator can determine from the number of response pulses counted over the selected period of time and the number of pulses generated by the auditory stimulus generator during the selected period of time a measure of the likelihood that a response is being evoked in a subject by the auditory signals.

3. Apparatus for generating data from which the likelihood of hearing impairment can be determined in a human subject who receives a selected auditory signal and whose response thereto is detected by an electroencephalographic transducer, comprising:
   (a) a bandpass filter having a frequency pass band containing the frequency of the component of the electroencephalographic signal expected as a response to the selected auditory signal in the subject being tested;
   (b) sampling means for sampling the polarity of the filtered electroencephalographic signal at predetermined times after the time of application of the selected auditory signal which correspond to the positive and negative peaks of the waveform of the expected response component, said sampling means providing a response output pulse when the polarity of the sampled signal matches the polarity of the expected response waveform at the predetermined time and also providing a trial output pulse at the time of each sample;
   (c) synchronizing means responsive to the auditory signal for triggering the sampling means at predetermined times after the auditory signal;
   (d) a response counter receiving the response output pulses from said sampling means and counting the pulses received by it and providing an output signal which is indicative of the total number of pulses counted; and
   (e) a trial counter receiving the trial output pulses from said sampling means and counting the number of pulses received by it and providing an output signal indicative of the total number of pulses counted, whereby an operator can determine the ratio of the number of response pulses to the number of trial pulses over a selected period of time to provide a measure of the likelihood that a response is being evoked in a subject by the auditory signals.

4. The apparatus of claim 1 or 3 including means for comparing the count total in said trials counter with a predetermined trials count and for issuing an output signal to terminate counting when the predetermined trials count is obtained.

5. The apparatus of claim 3 including an auditory stimulus generator adapted to provide auditory signal pulses to the ear of the human subject at uniform frequency.

6. The apparatus of claim 4 including control logic means connected to receive the output signal from said means for comparing the count in said trials counter and also receiving the response pulses and trials pulses outputs of said sampling means, said control logic means transmitting said response pulses and said trial pulses to said response and trials counters respectively as long as no signal is received from said means for comparing the count in said trials counter and blocking the passage of the response pulses and trials pulses when a signal is received from said means for comparing the count in said trials counter.

7. The apparatus of claim 1 or 3 including means for displaying to an operator the number of trials counted by said trials counter and means for displaying the number of responses counted by said response counter.

8. Apparatus for generating data from which the likelihood of hearing impairment can be determined in a human subject who receives a selected auditory signal and whose response thereto is detected by an electroencephalographic transducer, comprising:
   (a) an auditory stimulus generator adapted to provide auditory signal pulses to the ear of the human subject at a uniform frequency.
   (b) a bandpass filter having a frequency pass band containing the frequency of the component of the electroencephalographic signal expected as a response to the selected auditory signal in the subject being tested;
   (c) sampling means for sampling the polarity of the filtered electroencephalographic signal at predetermined times after the time of application of the selected auditory signal which correspond to the positive and negative peaks of the waveform of the expected response component, said sampling means providing a response output pulse when the polarity of the sampled signal matches the polarity of the expected response waveform at the predetermined time;
   (d) synchronizing means responsive to the auditory stimulus generator to trigger the sampling means at the predetermined times following the auditory signals; and
   (e) a response counter receiving the response output pulses from said sampling means and counting the pulses received by it over a selected period of time and providing an output signal which is indicative of the total number of pulses counted, whereby an operator can determine from the number of response pulses counted over the selected period of time and the number of auditory signal pulses over the selected period of time a measure of the likelihood that a response is being evoked in a subject by the auditory signals.

9. The apparatus of claim 1, 2, 3 or 8 including means for comparing the count total in said response counter with a predetermined response count and for issuing an output signal to terminate counting when the predetermined response count is obtained.

10. The apparatus of claim 8 or 5 wherein said auditory stimulus generator comprises:
    (1) an audio frequency oscillator;
    (2) an electronic gate receiving the signal from said audio frequency oscillator and passing the signal therethrough at a magnitude proportional to the gating pulse received by said gate;
    (3) a gate generator providing gating pulses of selected duration to said electronic gate at selected time intervals, said gate generator adapted to be connected and sychronized to a clock oscillator to which said sampling means is sychronized, the output of said gate being adapted to be provided to an earphone worn by the subject being tested.

11. The apparatus of claim 10 wherein said audio frequency oscillator generates an audio frequency at approximately 1,000 Hz, wherein the gating pulses provided by said gate generator to said electronic gate are approximately 8.5 milliseconds in duration and have a 2 millisecond ramp rise time and a 2 millisecond ramp decay time, and wherein the gating pulses are provided at a frequency of approximately 12.5 Hz.

12. The apparatus of claim 8 or 5 wherein said bandpass filter substantially attenuates the frequencies of signals provided to it below approximately 25 Hz and above 100 Hz, and wherein said sampling means samples at times which are approximately 30, 41, 51 and 64 milliseconds after the auditory signal is provided by said auditory stimulus generator to an adult subject.

13. The apparatus of claim 8 or 5 wherein said bandpass filter substantially attenuates the frequencies of signals provided to it below approximately 25 Hz and about 100 Hz, and wherein said sampling means samples at times which are approximately 28, 38, 54, and 71 milliseconds after the auditory signal is provided by said auditory stimulus generator to an infant subject.

14. The apparatus of claim 3 or 8 including a clock oscillator providing uniform clock pulses and wherein said sampling means includes:
    (1) a comparator which receives the filtered electroencephalographic signal from said band pass filter and provides a signal positive output on a first line which is in a logical high state when the input signal to the comparator is positive in polarity and is low otherwise, and a signal negative output on a second line which provides a logical high when the input to the comparator is negative in polarity and is low otherwise;
    (2) adjustable delay means, receiving clock pulses from said clock oscillator which are synchronized to the pulses of the auditory stimulus provided to the subject, and having four outputs, for providing a pulse on a first of said outputs a selected period of time after each clock pulse which corresponds in time to the first positive peak in the expected waveform, providing a pulse on a second of said outputs corresponding to the time of the first negative peak in the expected response waveform, providing a pulse on a third of its outputs corresponding to the time of the second positive peak in the expectd response waveform, and providing a pulse on a fourth of its outputs at a time corresponding to the second negative peak in the expected response waveform;
    (3) logic means for combining the outputs of said comparator and said adjustable delay means and providing a response output which is at a logical high level when a pulse is present on the first or third of said adjustable delay outputs and a pulse is present on said signal positive output of said comparator or when a pulse is present on said second and fourth outputs of said adjustable delay means and a pulse is present on said signal negative output of said comparator, and wherein said logic means also provides a trials output which is at a logical high level when any of the outputs of said adjustable delay means are at a logical high level.

15. The apparatus of claim 3 or 8 including control logic means connected to receive the output signal from said means for monitoring the count in said responses counter and also receiving the response pulse output of said sampling means, said control logic means transmitting said response pulses to said response counter as long as no signal is received from said means for comparing the count in said response counter and blocking the passage of the response pulses when a signal is received from said means for comparing the count in said response counter.

16. The apparatus of claim 2 or 8 including means for displaying to an operator the number of responses counted by said response counter.

17. The apparatus of claim 1, 2, 3 or 8 further including automatic gain control means receiving the signal from the electroencephalographic transducer and stabilizing the average magnitude of the signal to a predetermined level.

18. The apparatus of claim 17 further including an overload detector which monitors the level of the electroencephalographic signal from the transducer and issues a logical high output when no overload is present and a logical low output when an overload is present, said apparatus further including an underload detector which issues a logical high output when the average electroencephalographic signal is above a predetermined level and issues a logical low output when the average electroencephalographic signal is below a predetermined level; an AND gate which ands the outputs of said overload and underload detectors, the output of said AND gate provided to another input of another AND gate which has as its second input the trials pulses output, the output of said AND gate being further provided to the input of another AND gate which has its other input as the responses pulses output line, whereby the output of said last AND gate will correspond to the response pulses only if no overload and no underload is present in the electroencephalographic signal.

19. The apparatus of claim 3 or 8 including an electroencephalographic transducer attachable to a subject to be tested and providing its output to said bandpass filter.

20. A method of generating data which can be used to determine whether a human subject is capable of responding to auditory stimuli without requiring voluntary cooperation by the subject, comprising the steps of:
  (a) providing a series of auditory stimulus pulses to the ear of the subject during a test period;
  (b) detecting the electroencephalographic response of the subject to the stimulus pulses and providing an electrical signal corresponding thereto;
  (c) sampling the polarity of the electroencephalographic signal at predetermined times after the time of application of the auditory stimulus pulses to determine whether the polarity of the sampled signal matches the polarity of the waveform of the expected response component of the electroencephalographic signal at the time of the sample;
  (d) counting the total number of matches of the polarity of the electroencephalographic signal with the polarity of the expected waveform over the period of the test;
  (e) counting the total number of trials at which the electroencephalographic signal was sampled during the test.

21. A method of generating data which can be used to determine whether a human subject is capable of responding to auditory stimuli without requiring voluntary cooperation by the subject, comprising the steps of:
  (a) providing a series of auditory stimulus pulses to the ear of the subject during a test period;
  (b) detecting the electroencephalographic response of the subject to the stimulus pulses and providing an electrical signal corresponding thereto;
  (c) filtering out frequency components of the electroencephalographic signal above and below a pass band of frequencies containing the frequency of the waveform of the expected response component of the electroencephalographic signal to improve the signal to noise ratio of the filtered signal;
  (d) sampling the polarity of the filtered electroencephalographic signal at predetermined times after the time of application of the auditory stimulus pulses to determine whether the polarity of the sampled signal matches the polarity of the waveform of the expected response component of the electroencephalographic signal at the time of the sample;
  (e) counting the total number of matches of the polarity of the electroencephalographic signal with the polarity of the expected waveform over the period of the test;
  (f) counting the total number of trials at which the electroencephalographic signal was sampled during the test.

22. The method of claim 21 further including the steps of:
  calculating the ratio of the number of responses counted to the number of trials counted over the test;
  calculating a statistical confidence limit ratio of responses to trials at a selected confidence level, and
  comparing the ratio of responses to trials with the value of the confidence limit calculated to determine whether the ratio of responses to trials indicates that the hypothesis that a response is not present may be rejected with a probability of error determined by the confidence level selected.

* * * * *

UNITED STATES PATENT AND TRADEMARK OFFICE
CERTIFICATE OF CORRECTION

PATENT NO. : 4,275,744
DATED : June 30, 1981
INVENTOR(S) : Thornton, et al.

It is certified that error appears in the above-identified patent and that said Letters Patent are hereby corrected as shown below:

Column 2, line 6 "sample" should be --sampled--;

Column 4, line 49 "sample" should be --sampling--;

Column 4, line 50 "binominal" should be --binomial--;

Column 4, line 57 "means" should be --mean --;

Column 4, line 60 "binominal" should be --binomial--;

Column 5, line 54 "binominal" should be --binomial--;

Column 10, line 45 "factor" should be --faster--;

Column 14, line 27 "51" should be --52--;

Column 14, line 60 "expectd" should be --expected--.

Signed and Sealed this

Twelfth Day of January 1982

[SEAL]

Attest:

GERALD J. MOSSINGHOFF

Attesting Officer — Commissioner of Patents and Trademarks